United States Patent
Park et al.

(10) Patent No.: US 9,830,800 B2
(45) Date of Patent: Nov. 28, 2017

(54) EARLY WARNING OF NON-COMPLIANCE WITH AN ESTABLISHED WORKFLOW IN A WORK AREA

(71) Applicant: Intel Corporation, Santa Clara, CA (US)

(72) Inventors: Mi Sun Park, Hillsboro, OR (US); Lei Yang, Hillsboro, OR (US); Jung Woo, Portland, OR (US); Shahrokh Shahidzadeh, Portland, OR (US)

(73) Assignee: INTEL CORPORATION, Santa Clara, CA (US)

( * ) Notice: Subject to any disclaimer, the term of this patent is extended or adjusted under 35 U.S.C. 154(b) by 0 days.

(21) Appl. No.: 15/087,098

(22) Filed: Mar. 31, 2016

(65) Prior Publication Data

US 2017/0287313 A1    Oct. 5, 2017

(51) Int. Cl.
  *G08B 23/00* (2006.01)
  *G08B 21/24* (2006.01)

(52) U.S. Cl.
  CPC .................. *G08B 21/245* (2013.01)

(58) Field of Classification Search
  CPC .................. G08B 21/245; G06Q 10/0633
  USPC ................ 340/573.1, 572.1, 539.11
  See application file for complete search history.

(56) References Cited

U.S. PATENT DOCUMENTS

| | | | | |
|---|---|---|---|---|
| 8,558,701 B2* | 10/2013 | Wegelin | ............... | A47K 5/1217 340/573.1 |
| 8,994,537 B2* | 3/2015 | Pokrajac | ............... | G08B 21/245 222/23 |
| 9,147,334 B2* | 9/2015 | Long | ......................... | H04Q 9/00 |
| 9,483,930 B1* | 11/2016 | Haaland | .................. | G01P 15/18 |
| 2009/0224907 A1* | 9/2009 | Sinha | .................... | G08B 21/245 340/539.11 |
| 2013/0342349 A1* | 12/2013 | Cruz | ..................... | G08B 21/245 340/573.1 |

* cited by examiner

*Primary Examiner* — Toan N Pham
(74) *Attorney, Agent, or Firm* — Finch & Maloney PLLC

(57) ABSTRACT

A system for early warning of non-compliance with an established workflow in a work area includes a radio frequency (RF) sensor configured to detect each of a plurality of RF signals located within the work area, and a monitoring system operably connected to the RF sensor. The monitoring system is configured to compare a temporal sequence of detected RF signals to a predetermined temporal sequence of the RF signals associated with the established workflow, and to determine whether a warning condition exists based on the comparison. The RF signals can be emitted by RFID tags within the work area, such as a patient room of a healthcare provider, and the RFID tags may be associated with a hand sanitizing station, an intravenous solution dispenser, and a healthcare provider staff member, each of which play a role in reducing the incidence of hospital-acquired infections through compliance with corresponding patient safety protocols.

25 Claims, 9 Drawing Sheets

EARLY WARNING OF NON-COMPLIANCE WITH AN ESTABLISHED WORKFLOW IN A WORK AREA

BACKGROUND

Certain facilities, such as healthcare facilities, factories, laboratories, and warehouses, are locations where people may be required or expected to follow certain established workflows or procedural protocols that are specific to the facility. For example, staff members at a healthcare facility may be required to follow certain health safety or hazard mitigation protocols for maintaining the safety of the staff, patients and visitors. In particular, some protocols are designed to reduce the sources of infections in patients who may have impaired immunity or are otherwise at a heightened risk of acquiring an infection. Hospitalized patients, for instance, are susceptible to hospital-acquired infection (HAI)—also known as nosocomial infection—which is an infection that is contracted from the environment or staff of a healthcare facility. HAIs can be spread in the hospital environment, nursing home environment, rehabilitation facility, clinic, or in other clinical settings. The United States Centers for Disease Control and Prevention (CDC) estimates that in American hospitals alone, there are roughly 1.7 million HAIs and 99,000 associated deaths each year. This estimation shows the severeness of HAIs and vulnerability in patient safety. HAIs can be caused by many factors, including the failure of healthcare facility staff to adhere to patient safety protocols, poor hygienic practices, and insufficiently sanitized medical equipment. Although protocols for reducing HAIs exist, certain tasks that have a high degree of impact on patient safety can still be overlooked, neglected, or otherwise not performed in accordance with these protocols, which unnecessarily increases the risk of infections in patients.

DETAILED DESCRIPTION

Figure 1:
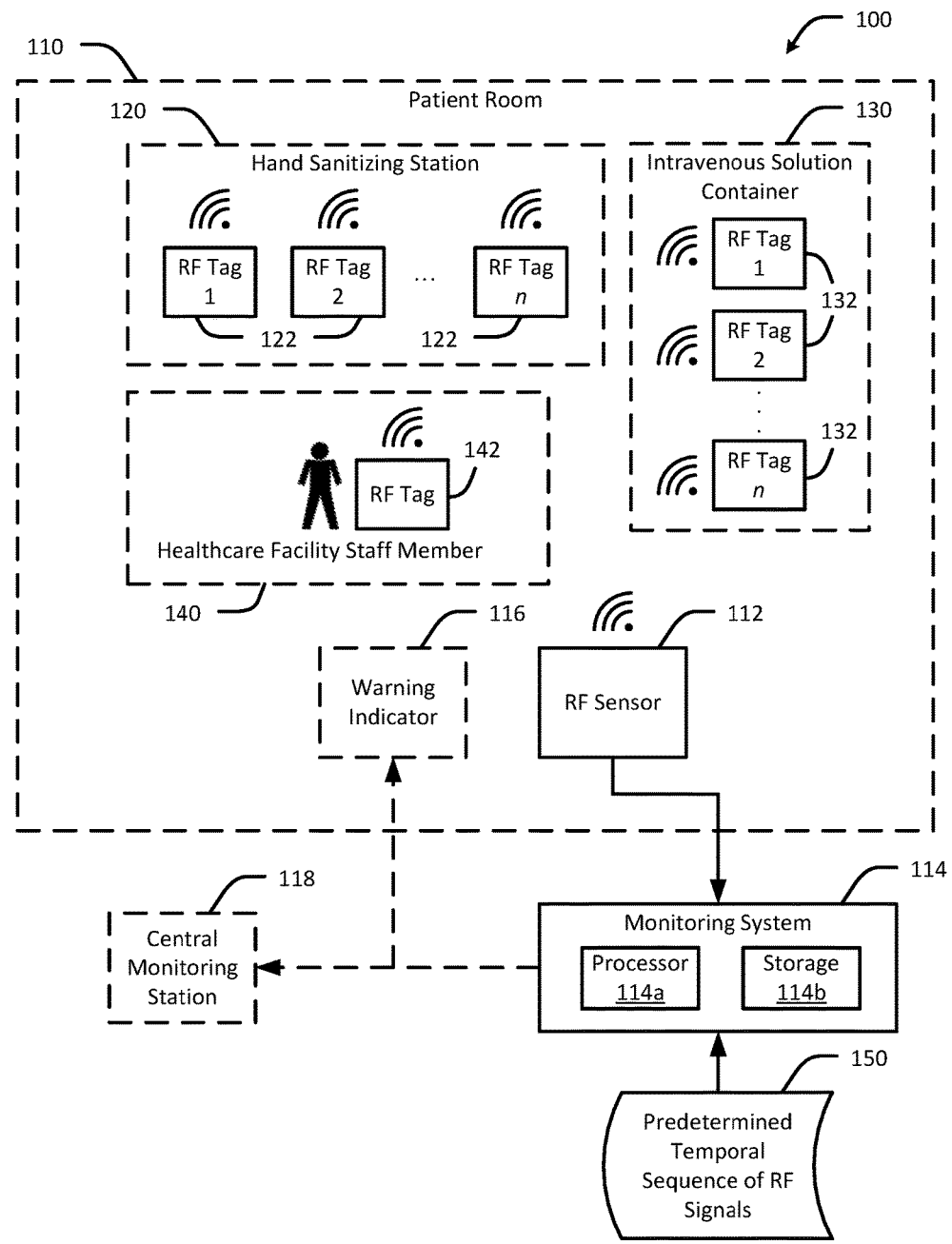
FIG. 1 shows an example early warning system for a facility, in accordance with an embodiment of the present disclosure.

As noted above, although protocols for reducing HAIs exist, certain tasks that have a high degree of impact on patient safety can still be overlooked, neglected, or otherwise not performed in accordance with these protocols, which unnecessarily increases the risk of infections in patients. As such, there is a need to improve patient safety by warning healthcare provider staff of avoidable errors before such errors lead to HAIs. In other situations, there are similar needs to warn people of avoidable errors resulting from the failure to comply with workflows established for a given facility (e.g., such as a machine shop where safety protocols with respect to using machinery must be followed by metal workers). For example, and in the context of a health facility, there are certain specific tasks that have a high impact on patient safety. These tasks include, for instance, detecting whether healthcare provider staff is following proper procedures, tracking hand sanitization of doctors and nurses before making physical contact with patients, and identifying the remaining level of intravenous (IV) solution available for a patient (e.g., ringer's solution or other liquid substance for treating a patient).

To this end, techniques are disclosed herein for providing an early warning of non-compliance with an established workflow in a work area of a given facility, such as a hospital patient room, nursing home, or other healthcare facility. The techniques can be implemented as a radio frequency identification (RFID)-based early warning system, according to one embodiment of the present disclosure. The system can detect (1) abnormal workflow of healthcare facility staff for reducing human error and adverse events, (2) hand-washing/sanitizing event for preventing hospital-acquired infection, and (3) the residual amount of medical intravenous solution for avoiding backflow of patient's blood. In addition, the system can provide an early warning to the healthcare facility staff to take appropriate action with respect to any or all such events. In the context of other types of facilities, the disclosed techniques can similarly improve compliance with established protocols by monitoring for abnormal workflows or other events, and providing warnings when such abnormal workflows or events occur.

According to some such embodiments, the early warning system includes a radio frequency (RF) sensor configured to detect each of a plurality of RF signals present within the healthcare facility patient room, and a monitoring system operably connected to the RF sensor. The RF signals can be signals emitted by one or more RFID tags within the patient room, including, for example, RFID tags associated with a hand sanitizing station, an intravenous solution dispenser, and a healthcare facility staff member, each of which play a role in reducing the incidence of HAIs through compliance with corresponding patient safety protocols. As will be appreciated in light of this disclosure, the early warning system, in general, takes advantage of the blocking or attenuation of RF signals caused by the presence of a human body (as in the case of a person occupying the hand sanitizing station or other station to be used in a given workflow), or the presence of a liquid (as in the case of a solution in the intravenous solution container). So, for instance, the system can determine whether any RFID tag signals are blocked or attenuated based on which signals are not detected by the RF sensor, or by the transition of signals from detected to undetected. Each of these signal types has a unique signature, and can therefore be uniquely identified. The monitoring system is configured to compare a temporal sequence of the RF signals detected by the RF sensor to a predetermined or expected temporal sequence of the RF signals associated with a patient treatment protocol. Based on this comparison, the early warning system can alert the healthcare facility staff member of any non-compliance with the established workflow. Numerous configurations and variations of such techniques will be apparent in light of this disclosure.

Example System

FIG. 1 shows an example early warning system 100 for a facility, in accordance with an embodiment of the present disclosure. In this example embodiment, the facility includes a healthcare facility patient room 110 (intended to include a room in any healthcare facility, including patient rooms in nursing homes, clinics, hospitals, skilled nursing facilities, etc); however, it will be understood that variations of the early warning system 100 described herein can be implemented in other types of facilities, such as warehouses, factories, laboratories, and other facilities having an established workflow, as will be apparent in light of this disclosure. Further note that the workflow may exist for safety purposes or some other purpose, such as compliance with government regulations. The system 100 includes an RF sensor 112 and a monitoring system 114 operatively connected to the RF sensor 112. In some embodiments, the RF sensor 112 can be any commercially available RFID reader having a beam-forming antenna array configured for RFID localization. The RF sensor 112 may include software or firmware that can be executed on an edge device such as Intel Edison or Raspberry Pi for each patient room, or on a backend server to process aggregated RFID data analytics across several patient rooms. In some embodiments, the system 100 further includes a warning indicator 116 and/or a central monitoring station 118 operatively connected to the monitoring system 114.

The patient room 110, or another facility, includes one or more RFID tags, as will be described in further detail below. The RFID tags may, for example, be relatively low cost wireless devices typically used in tracking, identification, and communication. Each of the RFID tags is configured to emit an RF signal that is detectable by the RF sensor 112. The RF signal emitted by each RFID tag may, for example, be encoded to include information that can be used to uniquely identify the RFID tag and/or provide other data generated by the tag. The RFID tags may include circuits that have a processor, a memory, an analog to digital converter/digital to analog converter, and an antenna. The RFID tags may be classified as passive or active, where passive RFID tags rely on an external power supply and active RFID tags include a power supply. The RFID tags may be associated with people or objects, and may be placed in fixed locations or freely moved about the patient room 110 or other facility, depending on a particular application.

According to an embodiment, the system 100 can be adapted for use in the patient room 110 by placing the RF sensor 112 in or proximate to the room, such as on the ceiling or a wall. Further, the RFID tags can be placed in several locations within the patient room 110. In one example, the patient room 110 includes a hand sanitizing station 120, an intravenous solution container 130, or both. As will be described in further detail below with respect to FIG. 3, the hand sanitizing station 120 includes one or more RFID tags 122 that are configured to emit RF signals detectable by the RF sensor 112. Similarly, as will be described in further detail below with respect to FIG. 5, the intravenous solution container 130 includes one or more RFID tags 132 that are also configured to emit RF signals detectable by the RF sensor 112. The RFID tags 122, 132 may, for example, be passive ultra-high frequency (UHF) RFID tags, although it will be understood that alternative frequencies, including high frequencies (HF) and low frequencies (LF) can also be used. It will also be understood that passive RFID tags, active RFID tags, battery-assisted passive RFID tags, or any combination of these types of RFID tags can be used. In some embodiments, UHF is generally understood to be in the range of 300 MHz to 3 GHz, HF is generally understood to be in the range of 3 MHz to 30 MHz, and LF is generally understood to be in the range of 30 KHz to 300 KHz, although other frequency ranges can also be used.

A healthcare facility staff member 140, or other individual, may from time to time enter the patient room 110, or other facility, in the course of performing certain duties, such as attending to a patient in the room. The healthcare facility staff member 140 carries on his or her person at least one RFID tag 142 (e.g., a passive UHF RFID tag). The RFID tag 142 is configured to emit an RF signal detectable by the RF sensor 112 while the RFID tag 142 is within range of the RF sensor 112. The RFID tag 142 carried by the healthcare facility staff member 140 or other individual is configured to provide, via the RF signal, information that is associated with the individual carrying the RFID tag 142. In this manner, the monitoring system 114 can generally determine the presence or absence of a particular healthcare facility staff member 140 in the patient room 110 or other facility based on the presence or absence of the RF signal emitted by the RFID tag 142, as detected by the RF sensor 112 and provided to the monitoring system 114. In some embodiments, the RFID tag 142 can be incorporated into a personnel identification badge or other object that is assigned to and generally carried by the particular healthcare facility staff member 140 as that individual conducts his or her duties within the healthcare facility or other facility.

As will be described in further detail below, the RF sensor 112 is configured to detect one or more RF signals emitted by any of the RFID tags, and in particular, any of the RFID tags that are located in the patient room 110 or other facility proximate to the RF sensor 112. The RF sensor 112 is further configured to provide information about the detected RF signals to the monitoring system 114. This information may include, for example, any of the information encoded in the RF signal, such as a unique identification number associated with the particular RFID tag, as well as the strength of the respective RF signal detected by the RF sensor 112 (e.g., a received signal strength indicator, or RSSI). In the course of detecting the RF signals, some of the RF signals may be detected at particular points in time, and in particular temporal sequences that define a sequence of events over space of time. For example, and as will be described in further detail below, an RF signal emitted by the RFID tag 142 of the healthcare facility staff member 140 may be detected by the RF sensor 112 while the RFID tag 142 is present in the patient room 110, indicating the presence of the healthcare facility staff member in the room at one or more points in time.

In turn, the monitoring system 114 is configured to compare the temporal sequence of the RF signals detected by the RF sensor 112 to a predetermined or expected temporal sequence of RF signals 150, and conditionally determine whether a warning condition exists based on the comparison. For example, the predetermined temporal sequence of RF signals 150 may be associated with a patient treatment regimen, patient safety protocol, or other established workflow for the work area. In such cases, a warning condition may exist when the RF signals are detected by the RF sensor 112 in a temporal sequence that is different from, or the same as, the predetermined temporal sequence, indicating that the regimen, protocol or workflow is or is not occurring in the expected sequence, as the case may be. Such a warning may be provided to the healthcare facility staff member 140 or other individual(s) by the monitoring system 114 in the form of a human-perceptible audible or visual cue so that the appropriate personnel are alerted to take corrective actions to avoid errors and to comply with the established patient treatment regimens, safety protocols, or other workflow associated with the facility, as the case may be. In addition to providing warnings, in some embodiments the monitoring system 114 can be configured to generate an audit trail that includes various events (both historical and forecast) relating to RF signal detection and other information, such as the date and time of the event and the identification of any healthcare facility staff members detected in the patient room 110.

In some embodiments, the warning indicator 116 is a device configured to generate an audible and/or visual cue to alert the healthcare facility staff member 142 or another individual of the existence of a warning condition. For example, the warning indicator 116 may include a lamp in the patient room 110 that turns on or flashes to indicate a warning, an enunciator or loudspeaker in the patient room 110 that emits a tone or other audible sound to indicate a warning, or both. In another example, the existence of a warning condition may be provided by the monitoring system 114, in the form of an electronic message or other signal, to the central monitoring station 118, which may be monitored by personnel delegated with the responsibility of managing the healthcare facility staff member 140 or other individuals. Such a message or signal may, for example, include a series of tones and/or text messages including the room number and a description of the warning condition, such as "hand sanitization warning" or "low residual IV solution warning." The message or signal may be provided via a wired or wireless communication network. In yet another example, the warning may be provided by the monitoring system 114 in the form of a text or voice message to a pager, smartphone, or other mobile device carried by the healthcare facility staff member 140 or other individual. In some embodiments, a warning signal or other information processed by the monitoring system 114 can be provided to the healthcare facility staff member 140 or other individual via an application or user interface designed to execute on a smartphone or other computing device.

Figure 2:
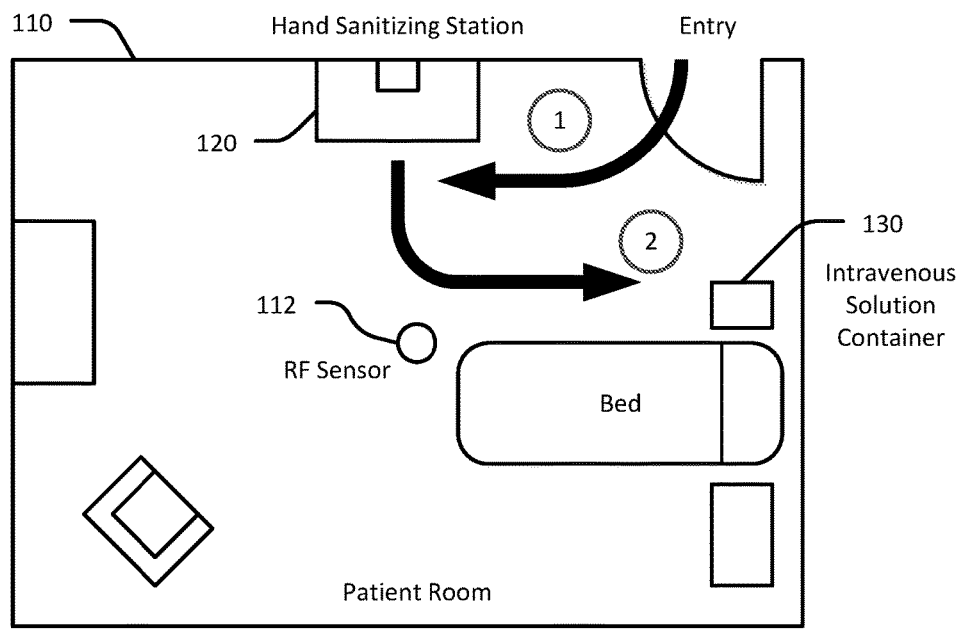
FIG. 2 shows a schematic of an example patient room of a healthcare facility, in accordance with an embodiment of the present disclosure.

FIG. 2 shows a schematic of an example healthcare facility patient room 110, in accordance with an embodiment of the present disclosure. As described above with respect to FIG. 1, the patient room 110 can include the RF sensor 112, as well as the hand sanitizing station 120, the intravenous solution container 130, or both. The RF sensor 112 may be located, for example, on the ceiling of the room, on one of the walls, or in another suitable location. In some embodiments, the RF sensor 112 includes multiple antennas mounted at various different locations. For example, the RF sensor 112 may include at least three antennas located such that trilateration techniques can be used to determine the position of an RFID tag relative to the RF sensor 112, as will be understood by one of skill in the art. The hand sanitizing station 120 may be located, for example, on or adjacent to a wall of the patient room 110, and more particularly, near the entryway of the room for convenient access to people who are entering the room. The hand sanitizing station 120 may include, for example, a dispenser configured to dispense a sanitizing solution, such as an antiseptic or disinfectant designed for cleaning hands, and/or the hand sanitizing station 120 may include a sink and faucet or other washing facilities for cleaning hands. The intravenous solution container 130 may, for example, be located near a bed in the patient room 110, although it will be understood that the container may be mounted on a portable rack or frame to provide for patient mobility within the room.

Still referring to FIG. 2, according to an embodiment, an example patient safety protocol prescribes that any healthcare facility staff member 140 entering the patient room 110 visit the hand sanitizing station 120 to sanitize his or her hands before making any contact with the patient in the room, as indicated by the arrows labeled "1" and "2", respectively. An example patient treatment regimen may, in addition to or instead of the patient safety protocol, prescribe that the intravenous solution container 130 be replaced before the residual amount of intravenous solution in the container falls below a certain volume (e.g., to prevent backflow of the patient's blood into the IV tube), or if the rate at which the intravenous solution dispenses out of the container is too fast or too slow for a particular medical therapy. With such a treatment regimen, the monitoring system 114 can be configured to determine, by detecting various RFID tags with the RF sensor 112, 1) when the healthcare facility staff member 140 enters the patient room 110; 2) whether or not the healthcare facility staff member 140 visits the hand sanitizing station 120 within a predetermined amount of time after entering the room (e.g., within 10, 20 or 30 seconds of entry); 3) whether or not the healthcare facility staff member 140 has properly sanitized his or her hands before attending to the patient based on the amount of time he or she is at the hand sanitizing station 120 (e.g., 5 or 10 seconds); 4) whether or not the residual amount of intravenous solution in the intravenous solution container 130 has fallen below a predetermined volume; 5) whether or not the intravenous solution is dispensing out of the container too quickly or too slowly, or any combination of these. Such determinations using the RFID tags will now be variously described in further detail with respect to FIGS. 3, 4A, 4B, 4C and 5.

Figure 3:
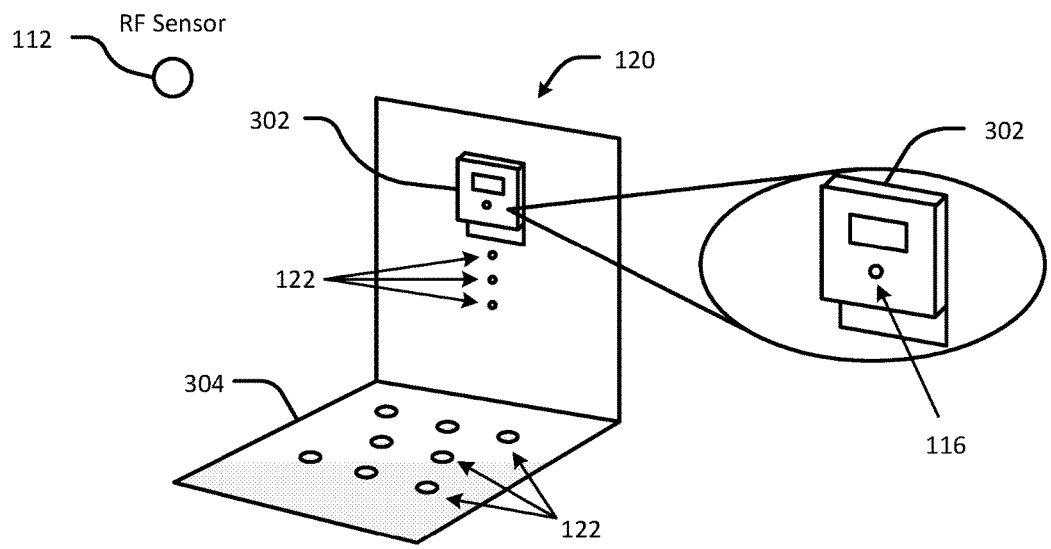
FIG. 3 shows a perspective view of an example hand sanitizing station in further detail, in accordance with an embodiment of the present disclosure.

FIG. 3 shows a perspective view of the hand sanitizing station 120 in further detail, in accordance with an embodiment of the present disclosure. In this example, the hand sanitizing station 120 includes, as mentioned above, a dispenser 302 configured to dispense a sanitizing solution, such as an antiseptic or disinfectant designed for cleaning hands, and/or a sink and faucet or other washing facilities for cleaning hands. The hand sanitizing station 120 further includes one or more of the RFID tags 122 variously mounted in or on the wall and the floor near the dispenser 302 or the sink. The RF sensor 112 is configured to detect any RF signals emitted by the RFID tags 122, such as described below with respect to FIGS. 4A, 4B and 4C. The example placement of the RFID tags 122 in FIG. 3 advantageously utilizes the multipath effects of the RF signals emitted by the RFID tags, since differential RF signal strengths and/or tag read rates from each of the RFID tags can be collected over a period of time to detect events caused by changes in the environment, such as occupation of the hand sanitizing station 120 by a healthcare facility staff member 140 or other individual. For instance, in accordance with various embodiments, it is appreciated that the human body has a significant impact on the ability to detect the RF signal emitted by an RFID tag when the body is between the RFID tag and the RF sensor 112 due to the absorption of RF signals by the body. When no one is obstructing the RF signal, both the signal strength and the average RFID tag read rate (e.g., the reception of RFID tag data via the RF signal emitted by the tag) are high. However, when someone is obstructing the RF signal, the average tag read rate is low or zero because the person's body is blocking the RF signal from reaching the RF sensor 112. Thus, according to this property, the presence or absence of a person at a particular location, such as the hand sanitizing station 120, can be determined based on the detection, or lack thereof, of the RF signals of one or more strategically located RFID tags, such as shown in FIG. 3. The level of confidence in detecting such events may be increased, for example, by increasing the number and/or variety of placement of the RFID tags near the hand sanitizing station 120. Thus, in the example of FIG. 3, the hand sanitizing station 120 may include approximately three RFID tags 122 on the wall and approximately eight RFID tags 122 on the floor, although it will be understood that the number and placement of RFID tags can vary from this example, as will be apparent in light of this disclosure.

In some embodiments, the hand sanitizing station 120 may include the warning indicator 116, such as a lamp that flashes or turns red to indicate that a warning condition exists (e.g., hands are not sanitized according to the patient safety protocol). In some embodiments, the warning indicator 116 may also include a lamp that turns green or otherwise indicates compliance with the patient safety protocol.

Figure 4A:
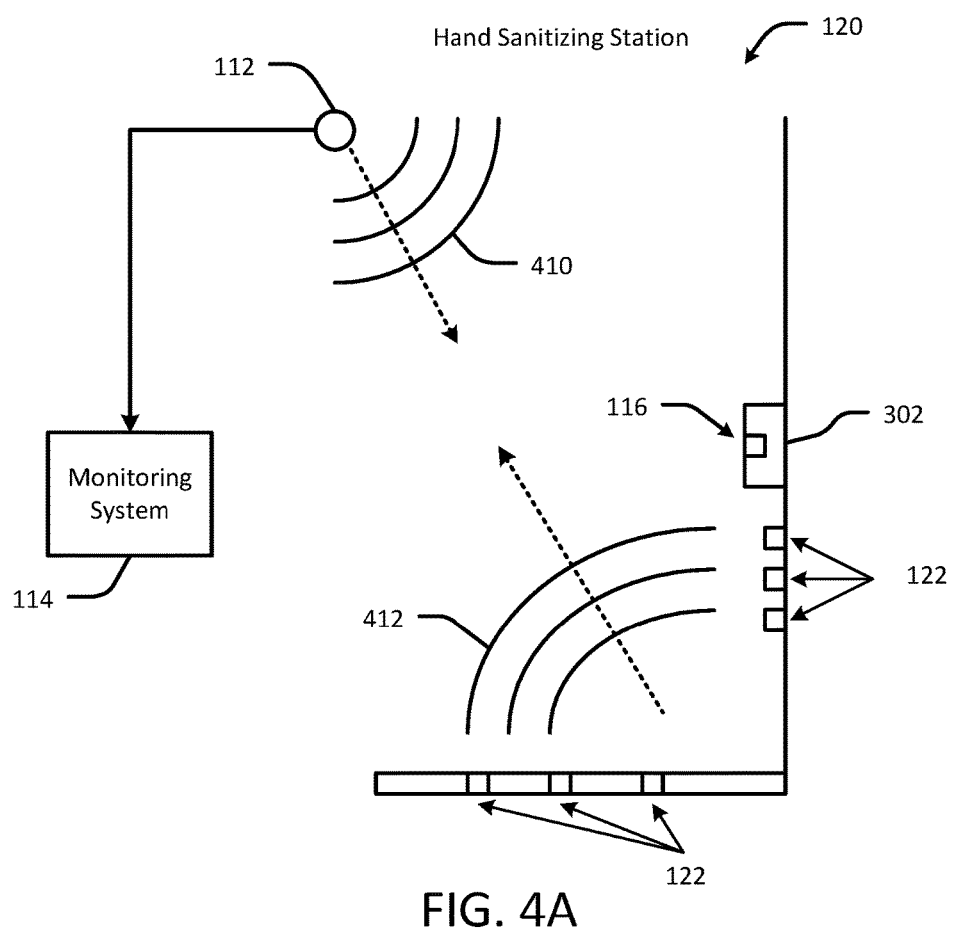
FIGS. 4A, 4B and 4C show examples of the hand sanitizing station of FIG. 3 in various stages of use, according to an embodiment of the present disclosure.
Figure 4B:
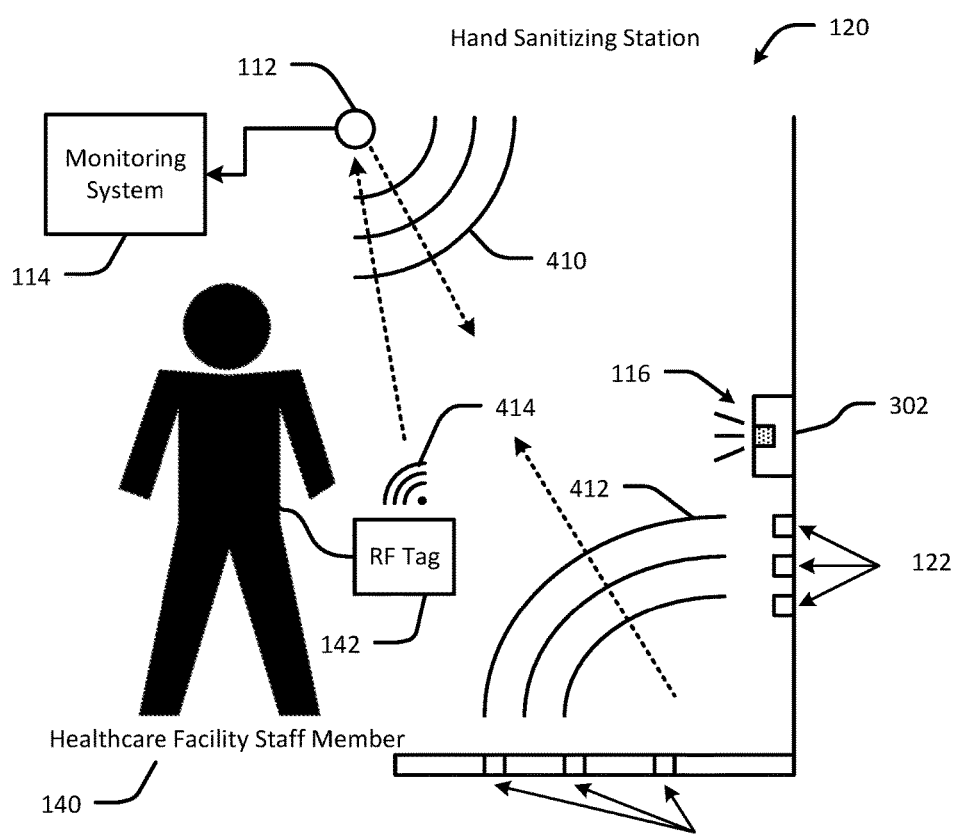
Figure 4C:
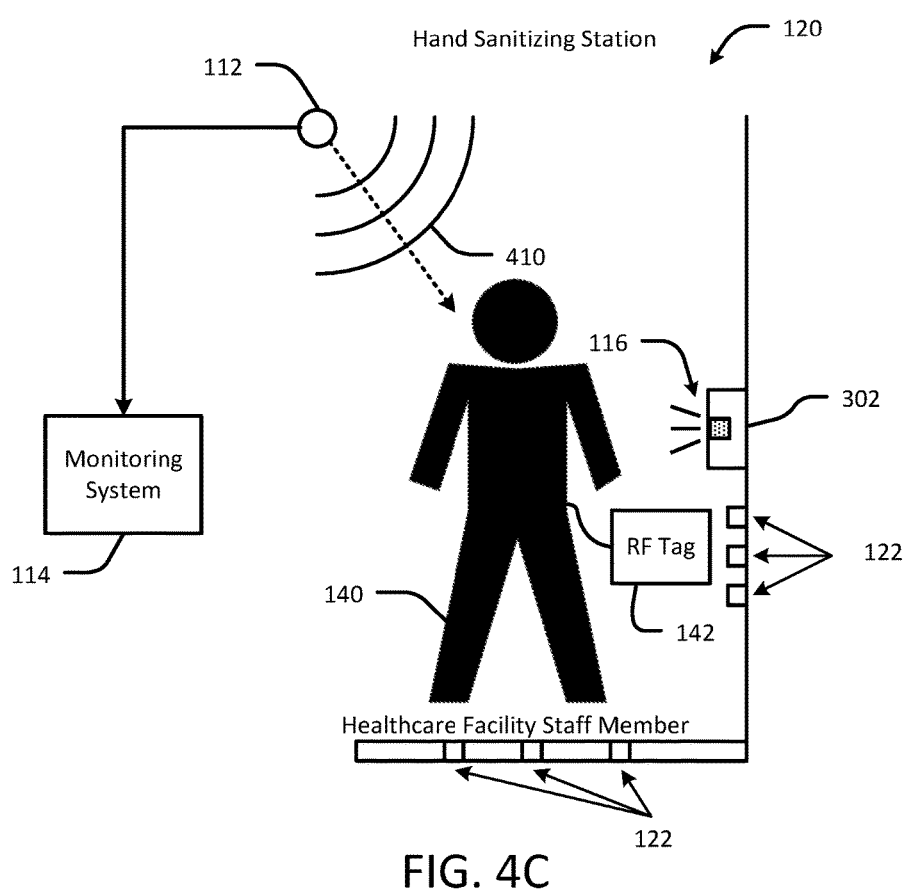

FIGS. 4A, 4B and 4C show examples of the hand sanitizing station 120 in various stages of use, according to an embodiment of the present disclosure. As mentioned above, in some embodiments the RF sensor 112 includes a beam-forming antenna array for RFID localization. The antenna array may, for example, be configured to radiate RF beams 410 in a pattern having at least three orientations (both horizontal and vertical paths), which permits detection of not only the presence of an RFID tag, but also the position of the RFID tag relative to the RF sensor 112 as well as the presence or absence of a person at a particular location due to the absorption of RF signals by the human body, as discussed above with respect to FIG. 3. For instance, the antenna array may be configured to radiate RF beams 410 in a pattern having 52 orientations; however, it will be understood that this is merely one example implementation, and that the number of orientations can be based on a given hardware implementation. As also discussed above with respect to FIG. 2, in some embodiments the facility may implement a patient safety protocol that prescribes, among other things, that any healthcare facility staff member 140 must visit the hand sanitizing station 120 to sanitize his or her hands before attending to the patient. Such a safety protocol can be represented, in some embodiments, by a predetermined, or expected, temporal sequence of RF signals from various RFID tags located in the patient room 110. For example, the predetermined temporal sequence of RF signals may represent the following timed-based sequence of RF signals:

T1—Unoccupied) No healthcare facility staff member RFID tags 142 are detected by the RF sensor 112 in the patient room 110. All hand sanitizing station RFID tags 122 are detected by the RF sensor 112, indicating that the hand sanitizing station 120 is unoccupied (high average tag read rates for all tags). See, for example, FIG. 4A.

T2—Pre-sanitizing) A healthcare facility staff member RFID tag 142 is detected by the RF sensor 112 in the patient room 110. All hand sanitizing station RFID tags 122 are detected by the RF sensor 112, indicating that the hand sanitizing station 120 is unoccupied (high average tag read rates for all tags). See, for example, FIG. 4B. T2 is expected to occur after T1.

T3—Sanitizing) Less than all of the hand sanitizing station RFID tags 122 are detected by the RF sensor 112, indicating that the hand sanitizing station 120 is occupied (low average tag read rates for at least some tags) while a person is using the sanitizer (and thereby blocking at least some of the RF signals). See, for example, FIG. 4C. T3 is expected to occur within a predetermined amount of time after T2 (e.g., within approximately 10, 20 or 30 seconds).

T4—Post-sanitizing) Average read rate of at least some of the hand sanitizing station RFID tags 122 is less than a threshold value (e.g., less than 98% of all tags) for at least some period of time after T3 occurs that is sufficient for a person to complete hand sanitizing (e.g., approximately 5 to 10 seconds after T3).

In FIG. 4A, the hand sanitizing station 120 is shown unoccupied. As a result, there are no physical obstructions between the RF sensor 112 and the RFID tags 122 associated with the hand sanitizing station 120, including the RFID tags mounted in or on the wall and the floor. This permits the RF sensor 112 to receive and detect RF signals 412 emitted by the RFID tags 112. As noted above, in some embodiments the RFID tags 112 are passive RFID tags that are configured to emit RF energy obtained from the RF beams 410. Generally, in this example, the signal strength, or RSSI, and/or average tag read rates of each of the RF signals 410 is high at the RF sensor 112, since there are no obstructions to either the outbound RF beams 410 or the inbound RF signals 412. The monitoring system 114 can determine whether the hand sanitizing station 120 is unoccupied when any of the RFID tags 112, with high RF signal strengths or high average tag read rates, are detected by the RF sensor 112 (e.g., event T1). The certainty that the hand sanitizing station 120 is unoccupied may depend, for example, on the number of RFID tags detected and the strength of each corresponding RF signal 412.

In FIG. 4B, the hand sanitizing station 120 is again shown unoccupied, as in FIG. 4A. However, the healthcare facility staff member 140 carrying an RFID tag 142 is present in the patient room 110. The monitoring system 114 can determine whether the healthcare facility staff member 140 has entered the patient room 110 when the RF sensor 112 first detects an RF signal 414 emitted by the RFID tag 142 (e.g., event T2). The monitoring system 114 can also determine whether the healthcare facility staff member 140 is not occupying the hand sanitizing station 120 because, as described with respect to FIG. 4A, the healthcare facility staff member 140 is not obstructing the RF signals 412 emitted by at least some, if not all, of the hand sanitizing station RFID tags 122. In this situation, the monitoring system 114 determine whether a warning condition exists (hand sanitization required) and, in some embodiments, the monitoring system 114 can further cause the warning indicator 116 to activate, which alerts the healthcare facility staff member 140 that he or she must visit the hand sanitizing station 120 before attending to the patient. For example, as soon as the monitoring system 114 determines that the healthcare facility staff member 140 has entered the patient room 110 (e.g., event T2), the monitoring system 114 may cause the warning indicator 116 to flash a red lamp, indicating that a warning condition exists. In another example, the monitoring system 114 may cause the warning indicator 116 to sound an audible alert if the monitoring system 114 determines that the healthcare facility staff member 140 has not occupied the hand sanitizing station 120 (such as described below with respect to FIG. 4C) within a predetermined amount of time after entering the room (e.g., 10, 20 or 30 seconds after entry).

In FIG. 4C, the hand sanitizing station 120 is shown occupied by the healthcare facility staff member 122. The monitoring system 114 can determine whether the healthcare facility staff member 140 is occupying the hand sanitizing station 120 because the staff member's body is blocking and absorbing at least some of the RF signals 412 (not shown in FIG. 4C) emitted by the hand sanitizing station RFID tags 122 (e.g., event T3), or, particularly in the case of passive RFID tags, because the staff member's body is blocking and absorbing at least some of the RF signals 410 emitted by the RF sensor 112. In some cases, depending on the locations of the RF sensor 112 and the healthcare facility staff member's RFID tag 142 while using the hand sanitizing station (e.g., such as when the tag is worn on a lanyard around the staff member's neck and he or she is facing away from the RF sensor 112), the RF sensor 112 may not be able to detect the healthcare facility staff member's RFID tag 142 because the staff member's body is blocking the RF signal. However, in such cases, the monitoring system 114 can remember that the healthcare facility staff member 140 has entered the room and can deduce that the person occupying the hand sanitizing station 120 is the staff member, even if the staff member's RFID tag 142 is not detected while the hand sanitizing station 120 is occupied.

After the hand sanitizing station 120 has been occupied for some period of time (e.g., 5 to 10 seconds), the monitoring system 114 can cause the warning indicator 116 to turn off or turn on a green lamp indicating compliance with at least a portion of the patient safety protocol related to hand sanitization (e.g., event T4). This period of time is the minimum amount of time a person needs to properly use the hand sanitizing station 120, and may vary depending on the sanitizer or soap dispensed by the hand sanitizing station. For example, certain antibacterial solutions may be effective after at least 5 to 10 seconds of use, while certain hand soaps may require a longer usage period. The monitoring system 114 can be configured accordingly. After hand sanitization is complete, the healthcare facility staff member 140 can proceed to attend to the patient, and the monitoring system 114 will not issue any further hand sanitization warnings until the healthcare facility staff member 140 exits the patient room 110, or after some amount of time has passed since the last time the monitoring system 114 determined that the hand sanitizing station 120 was occupied (e.g., 30 minutes, 1 hour, 2 hours, or another time interval).

Figure 5:
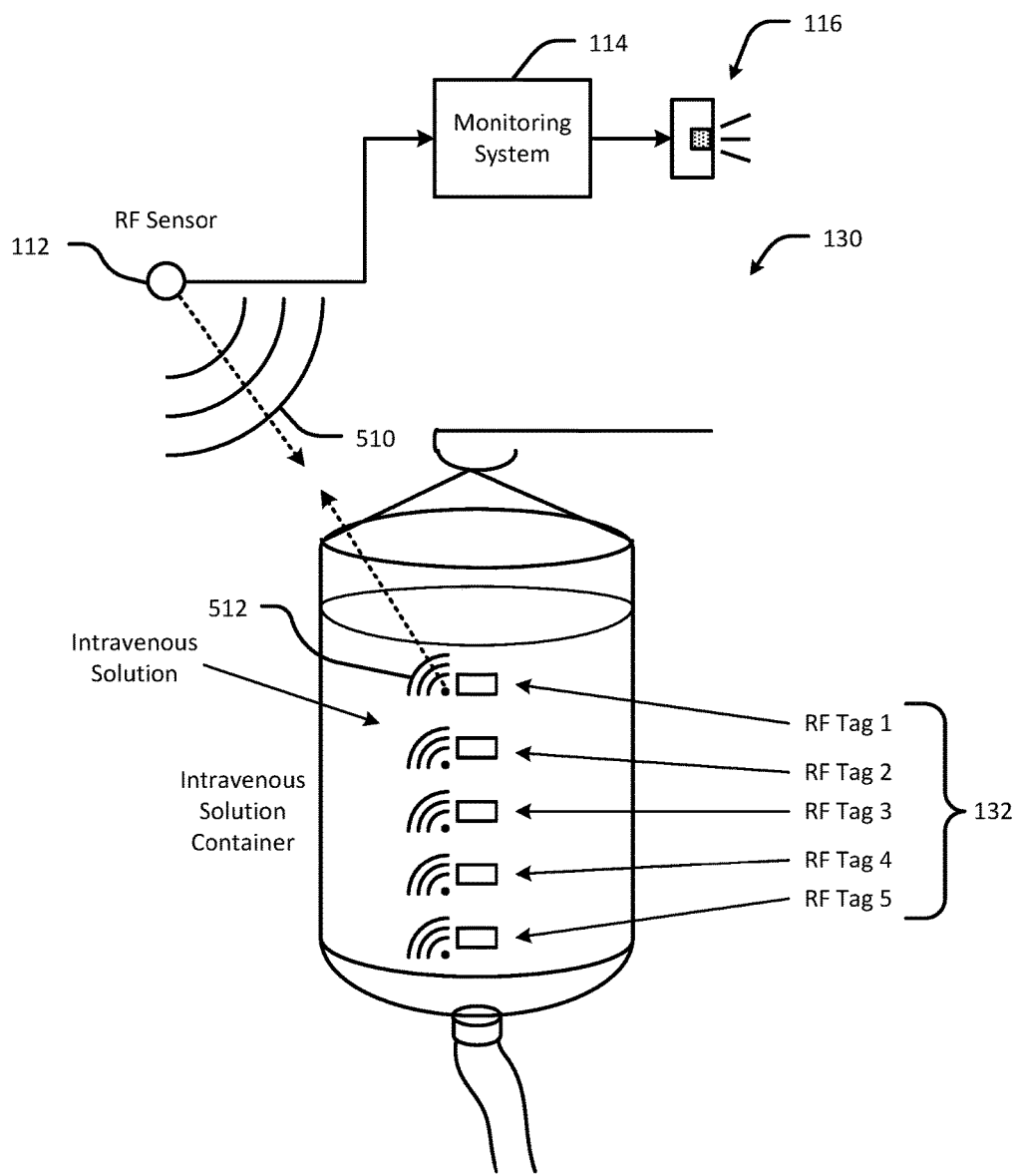
FIG. 5 shows a schematic view of an example intravenous solution container, in accordance with an embodiment of the present disclosure.

FIG. 5 shows a schematic view of the intravenous solution container 130, in accordance with an embodiment of the present disclosure. In this example, the intravenous solution container 130 includes one or more intravenous solution dispenser RFID tags 132 variously mounted on the container. The RF sensor 112 is configured to detect any RF signals 512 emitted by the RFID tags 132. For instance, in accordance with various embodiments, it is appreciated that a liquid, such as an IV solution, has a significant impact on the ability to detect the RF signal emitted by an RFID tag when the liquid is between the RFID tag and the RF sensor 112 due to the attenuation of RF signal strength and the absorption of RF signals by the liquid. When a liquid is obstructing the RF signal 512, the signal strength and/or the average RFID tag read rate (e.g., the reception of RFID tag data via the RF signal emitted by the tag) are low. However, when there is no liquid obstructing the RF signal, the average tag read rate is high because there is no signal obstruction between the RF tag 132 and the RF sensor 112. Thus, according to this property, the level of a liquid in the container 130 can be determined based on the detection, or lack thereof, of the RF signals of one or more strategically located RFID tags, such as shown in FIG. 5. For instance, several RFID tags 132 may be placed at different levels of the container 130 corresponding to different IV solution levels within the container. When the solution level is at or above an RFID tag, the solution attenuates strength of the RF signal emitted by that RFID tag, reducing the average read rate for that tag and indicating that the intravenous solution container 130 contains at least the corresponding amount of IV solution. Similarly, when the solution level is below an RFID tag, the strength of the RF signal emitted by that RFID tag is not attenuated, increasing the average read rate for that tag and indicating that the intravenous solution container 130 contains less than the corresponding amount of IV solution. The level of confidence in detecting the amount of residual solution in the container 130 may be increased, for example, by increasing the number and/or variety of placement of the RFID tags on the container 130. Thus, in the example of FIG. 5, the intravenous solution container 130 may include approximately five RFID tags 132 at different locations on the side of the container, although it will be understood that the number and placement of RFID tags can vary from this example, as will be apparent in light of this disclosure.

As also discussed above with respect to FIG. 2, in some embodiments the facility may implement a patient treatment regimen that prescribes, among other things, that an intravenous solution container be replaced when the residual amount of intravenous solution in the container falls below a certain level to prevent backflow of the patient's blood and to help prevent any HAIs. Such a regimen can be represented, in some embodiments, by a predetermined, or expected, temporal sequence of RF signals from various RFID tags located in the patient room 110. For example, the predetermined temporal sequence of RF signals may represent the following timed-based sequence of RF signals:

T1—IV Container Full) The average read rate of all intravenous solution container RFID tags 132 detected by the RF sensor 112 is very low (e.g., less than approximately 20%), indicating that the intravenous solution container 130 is full.

T2—IV Container Partially Full) The average read rate of all intravenous solution container RFID tags 132 detected by the RF sensor 112 is low (e.g., less than approximately 98%), indicating that the intravenous solution container 130 is partially full.

T3—IV Container Residual Level Low) The average read rate of all except one of the intravenous solution container RFID tags 132 detected by the RF sensor 112 is high (e.g., greater than or equal to approximately 98%), indicating that the residual amount of IV solution in the container 130 is below a given level.

In some embodiments, the monitoring system 114 can determine whether a warning condition exists by comparing a temporal sequence of the RF signals 512 detected by the RF sensor 112 to a predetermined temporal sequence of the RF signals associated with a patient treatment regimen, such as described above (e.g., T1 followed by T2 followed by T3). In some embodiments, the monitoring system 114 can measure the amount of time between each step in the sequence (e.g., the time between T1 and T2 and the time between T2 and T3) and determine whether a warning condition exists if any of the measured times are too short (indicating that the IV solution is dispensing too quickly) or too long (indicating that the IV solution is dispensing too slowly) for a given treatment regimen. In some embodiments, the monitoring system 114 can determine whether a warning condition exists if the intravenous solution container 130 is not filled at least once during a given time period (e.g., at least once every 30 minutes, 1 hour or 2 hours). In some embodiments, the monitoring system 114 is configured to cause the warning indicator 116 to generate an audible (e.g., a tone) or visual (e.g., a lamp) cue in response to determining that the warning condition exists.

Example Devices

Referring again to FIG. 1, monitoring system 114 includes a processor 114a and a storage 114b. The processor 114a can be any suitable processor, and may include one or more coprocessors or controllers to assist in control and processing operations associated with the monitoring system 114. The storage 114b can be implemented using any suitable type of digital storage, such as one or more of a disk drive, a universal serial bus (USB) drive, flash memory and/or random access memory (RAM). The processor 114a is configured to execute an operating system, which may include any suitable operating system, such as Linux, Google Android (Google Inc., Mountain View, Calif.), Microsoft Phone (Microsoft Corp., Redmond, Wash.), or Apple iOS (Apple Inc., Cupertino, Calif.). As will be appreciated in light of this disclosure, the techniques provided herein can be implemented without regard to the particular operating system provided in conjunction with processor 114a, and therefore may also be implemented using any suitable existing or subsequently-developed platform.

The various embodiments disclosed herein can be implemented in various forms of hardware, software, firmware, and/or special purpose processors. For example in one embodiment a non-transitory computer readable medium has instructions encoded thereon that, when executed by one or more processors, cause one or more of the methodologies disclosed herein to be implemented. The instructions can be encoded using a suitable programming language, such as C, C++, object oriented C, JavaScript, Visual Basic .NET, Beginner's All-Purpose Symbolic Instruction Code (BASIC), or alternatively, using custom or proprietary instruction sets. The instructions can be provided in the form of one or more computer software applications and/or applets that are tangibly embodied on a memory device, and that can be executed by a computer having any suitable architecture. In one embodiment, the system can be implemented, for example, using JavaScript or another suitable technology. The computer software methodologies disclosed herein may include any number of different modules, sub-modules, or other components of distinct functionality, and can provide information to, or receive information from, still other components. These modules can be used, for example, to communicate with input and/or output devices such as a display screen, a touch sensitive surface, a printer, and/or any other suitable device. Other componentry and functionality not reflected in the illustrations will be apparent in light of this disclosure, and it will be appreciated that other embodiments are not limited to any particular hardware or software configuration. Thus in other embodiments the system 100 may have additional, fewer, or alternative subcomponents as compared to those included in the example embodiment of FIG. 1.

The aforementioned non-transitory computer readable medium may be any suitable medium for storing digital information, such as a hard drive, a server, a flash memory, and/or random access memory (RAM). In alternative embodiments, the components and/or modules disclosed herein can be implemented with hardware, including gate level logic such as a field-programmable gate array (FPGA), or alternatively, a purpose-built semiconductor such as an application-specific integrated circuit (ASIC). Still other embodiments may be implemented with a microcontroller having a number of input/output ports for receiving and outputting data, and a number of embedded routines for carrying out the various functionalities disclosed herein. It will be apparent that any suitable combination of hardware, software, and firmware can be used, and that other embodiments are not limited to any particular system architecture.

Methodology

Figure 6:
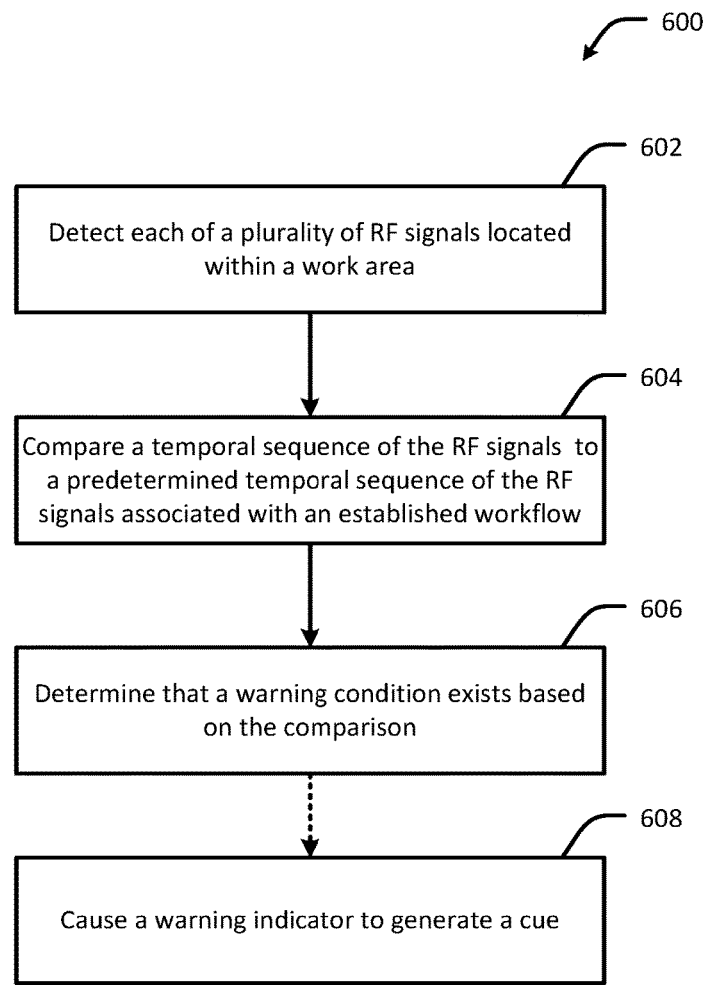
FIG. 6 shows a flow diagram representing an example methodology for providing an early warning in a patient room of a healthcare facility, in accordance with an embodiment of the present disclosure.

FIG. 6 shows a flow diagram representing an example methodology 600 for providing an early warning in a patient room or other work area, in accordance with an embodiment of the present disclosure. This example methodology 600 may, for example, be implemented in the early warning system 100 of FIG. 1. The method 600 begins by detecting 600 (e.g., by the radio frequency (RF) sensor 112 of FIG. 1), each of a plurality of radio frequency (RF) signals located within the patient room. As mentioned above, the RF signals may be signals emitted by one or more RFID tags (e.g., RFID tags 122, 132, 142 of FIG. 1). One or more of the RFID tags may be passive UHF RFID tags. The method 600 continues by comparing 604 (e.g., by the monitoring system 114 of FIG. 1), a temporal sequence of the RF signals detected by the RF sensor to a predetermined temporal sequence of the RF signals (e.g., the predetermined temporal sequence of RF signals 150 of FIG. 1) associated with an established workflow (e.g., a patient safety protocol or patient treatment regimen), and determining 606 (e.g., by the monitoring system 114 of FIG. 1) that a warning condition exists based on the comparison. In some embodiments, the method 600 includes causing 608 a warning indicator (e.g., the warning indicator 116 of FIG. 1) to generate a human-perceptible audible cue and/or a human-perceptible visual cue in response to determining that the warning condition exists. The method 600, or any steps thereof, may repeat indefinitely.

Figure 7:
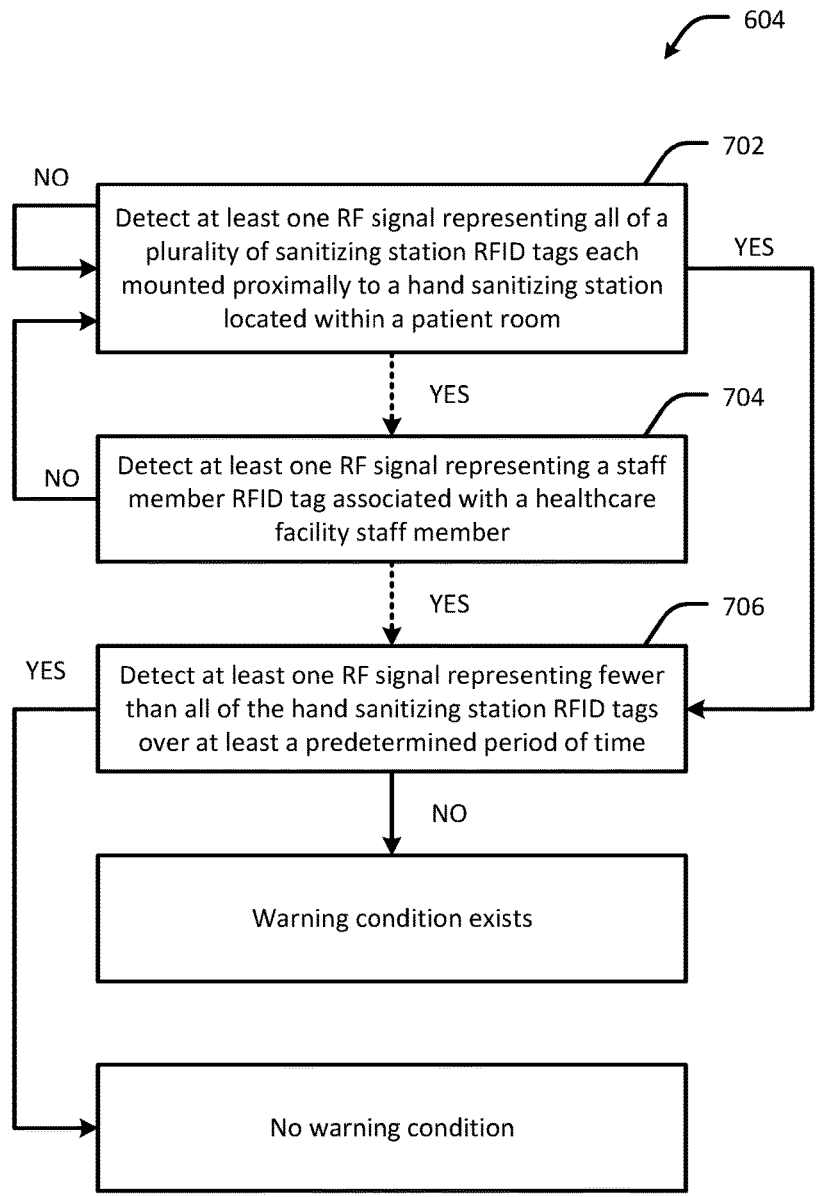
FIG. 7 shows a flow diagram representing an example methodology for a portion of the flow diagram of FIG. 6 in further detail, in accordance with an embodiment of the present disclosure.

FIG. 7 shows a flow diagram representing an example methodology for step 604 above in further detail, where the detected RF signals are emitted by one or more hand sanitizing station RFID tags, such as the RFID tags 122 described above with respect to FIGS. 1, 3, 4A, 4B and 4C. In this example embodiment, the warning condition exists while the temporal sequence of the RF signals detected by the RF sensor differs from the predetermined temporal sequence of the RF signals associated with the established workflow. Furthermore, the predetermined temporal sequence of the RF signals includes at least one RF signal representing all of a plurality of hand sanitizing station RFID tags each mounted proximally to a hand sanitizing station located within the patient room 702, followed by at least one RF signal representing fewer than all of the hand sanitizing station RFID tags over at least a predetermined period of time 706. In some embodiments, the predetermined temporal sequence of the RF signals further includes at least one RF signal representing a staff member RFID tag associated with a healthcare facility staff member 704, which occurs prior to the at least one RF signal representing fewer than all of the hand sanitizing station RFID tags 706. In this example, a warning condition exists if the temporal sequence of the RF signals detected by the RF sensor differs from the predetermined temporal sequence of the RF signals shown in FIG. 7, while no warning condition exists otherwise. Variations are possible and will be apparent in light of this disclosure.

Figure 8:
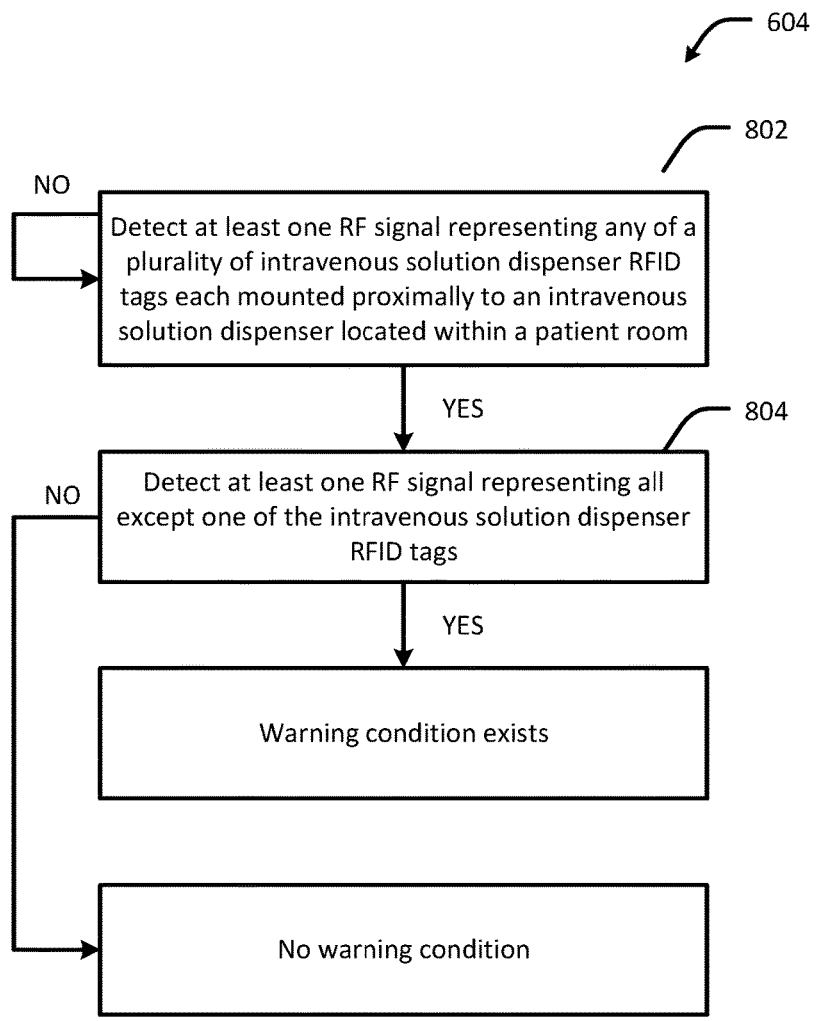
FIG. 8 shows a flow diagram representing another example methodology for a portion of the flow diagram of FIG. 6 in further detail, in accordance with an embodiment of the present disclosure.

FIG. 8 shows a flow diagram representing another example methodology for step 604 above in further detail, where the detected RF signals are emitted by one or more intravenous solution dispenser RFID tags, such as the RFID tags 142 described above with respect to FIGS. 1 and 5. In this example embodiment, the warning condition exists while the temporal sequence of the RF signals detected by the RF sensor is the same as the predetermined temporal sequence of RF signals associated with the established workflow. Furthermore, the predetermined temporal sequence of the RF signals includes at least one RF signal representing any of a plurality of intravenous solution dispenser RFID tags 802, followed by at least one RF signal representing all except one of the intravenous solution dispenser RFID tags 804. In this example, a warning condition exists if the temporal sequence of the RF signals detected by the RF sensor is the same as the predetermined temporal sequence of the RF signals shown in FIG. 8, while no warning condition exists otherwise. Variations are possible and will be apparent in light of this disclosure.

Various embodiments may be implemented using hardware elements, software elements, or a combination of both. Examples of hardware elements may include processors, microprocessors, circuits, circuit elements (for example, transistors, resistors, capacitors, inductors, and so forth), integrated circuits, ASICs, programmable logic devices, digital signal processors, FPGAs, logic gates, registers, semiconductor devices, chips, microchips, chipsets, and so forth. Examples of software may include software components, programs, applications, computer programs, application programs, system programs, machine programs, operating system software, middleware, firmware, software modules, routines, subroutines, functions, methods, procedures, software interfaces, application program interfaces, instruction sets, computing code, computer code, code segments, computer code segments, words, values, symbols, or any combination thereof. Determining whether an embodiment is implemented using hardware elements and/or software elements may vary in accordance with any number of factors, such as desired computational rate, power level, heat tolerances, processing cycle budget, input data rates, output data rates, memory resources, data bus speeds, and other design or performance constraints.

Some embodiments may be described using the expression "coupled" and "connected" along with their derivatives. These terms are not intended as synonyms for each other. For example, some embodiments may be described using the terms "connected" and/or "coupled" to indicate that two or more elements are in direct physical or electrical contact with each other. The term "coupled", however, may also mean that two or more elements are not in direct contact with each other, but yet still cooperate or interact with each other.

Some embodiments may be implemented, for example, using a machine readable medium or article which may store an instruction or a set of instructions that, if executed by a machine, may cause the machine to perform a method and/or operations in accordance with the embodiments. Such a machine may include, for example, any suitable processing platform, computing platform, computing device, processing device, computing system, processing system, computer, process, or the like, and may be implemented using any suitable combination of hardware and/or software. The machine readable medium or article may include, for example, any suitable type of memory unit, memory device, memory article, memory medium, storage device, storage article, storage medium, and/or storage unit, such as memory, removable or non-removable media, erasable or non-erasable media, writeable or rewriteable media, digital or analog media, hard disk, floppy disk, compact disk read only memory (CD-ROM), compact disk recordable (CD-R) memory, compact disk rewriteable (CR-RW) memory, optical disk, magnetic media, magneto-optical media, removable memory cards or disks, various types of digital versatile disk (DVD), a tape, a cassette, or the like. The instructions may include any suitable type of code, such as source code, compiled code, interpreted code, executable code, static code, dynamic code, encrypted code, and the like, implemented using any suitable high level, low level, object oriented, visual, compiled, and/or interpreted programming language.

Unless specifically stated otherwise, it may be appreciated that terms such as "processing", "computing", "calculating", "determining", or the like refer to the action and/or process of a computer or computing system, or similar electronic computing device, that manipulates and/or transforms data represented as physical quantities (for example, electronic) within the registers and/or memory units of the computer system into other data similarly represented as physical quantities within the registers, memory units, or other such information storage transmission or displays of the computer system. The embodiments are not limited in this context.

Numerous specific details have been set forth herein to provide a thorough understanding of the embodiments. It will be understood by an ordinarily-skilled artisan, however, that the embodiments may be practiced without these specific details. In other instances, well known operations, components and circuits have not been described in detail so as not to obscure the embodiments. It can be appreciated that the specific structural and functional details disclosed herein may be representative and do not necessarily limit the scope of the embodiments. In addition, although the subject matter has been described in language specific to structural features and/or methodological acts, it is to be understood that the subject matter defined in the appended claims is not necessarily limited to the specific features or acts described herein. Rather, the specific features and acts described herein are disclosed as example forms of implementing the claims.

Further Example Embodiments

The following examples pertain to further embodiments, from which numerous permutations and configurations will be apparent.

Example 1 is an early warning system for non-compliance with an established workflow in a work area. The system comprises a radio frequency (RF) sensor configured to detect each of a plurality of RF signals within the work area; and a monitoring system operably connected to the RF sensor, the monitoring system configured to: compare a temporal sequence of the RF signals detected by the RF sensor to a predetermined temporal sequence of the RF signals associated with the established workflow; and determine whether a warning condition exists based on the comparison.

Example 2 includes the subject matter of Example 1, further comprising at least one radio frequency identification (RFID) tag configured to emit at least one of the RF signals detectable by the RF sensor.

Example 3 includes the subject matter of Example 2, wherein the at least one RFID tag is one of an ultra-high frequency (UHF) RFID tag, a high frequency (HF) RFID tag, and a low frequency (LF) RFID tag.

Example 4 includes the subject matter of any of Examples 2 and 3, wherein the work area is a patient room of a healthcare facility, and the at least one RFID tag comprises at least one hand sanitizing station RFID tag mounted proximally to a hand sanitizing station located within the patient room.

Example 5 includes the subject matter of any of Examples 2-4, wherein the at least one hand sanitizing station RFID tag is mounted on one of a wall of the patient room and a floor of the patient room.

Example 6 includes the subject matter of any of Examples 2-5, wherein the work area is a patient room of a healthcare facility, and the at least one RFID tag comprises at least one intravenous solution RFID tag mounted proximally to an intravenous solution dispenser located within the patient room.

Example 7 includes the subject matter of Example 6, wherein the intravenous solution RFID tag is attached to a side of the intravenous solution dispenser.

Example 8 includes the subject matter of any of Examples 2-7, wherein the work area is a patient room of a healthcare facility, and the at least one RFID tag comprises a staff member RFID tag associated with a healthcare facility staff member and configured to be carried by the staff member while the staff member occupies the patient room.

Example 9 includes the subject matter of any of Examples 1-8, further comprising a warning indicator operably connected to the monitoring system and configured to generate a cue including at least one of a human-perceptible audible cue and a human-perceptible visual cue, wherein the monitoring system is further configured to cause the warning indicator to generate the cue in response to determining that the warning condition exists.

Example 10 includes the subject matter of any of Examples 1-9, wherein the warning condition exists while the temporal sequence of the RF signals detected by the RF sensor differs from the predetermined temporal sequence of the RF signals associated with the established workflow, thereby indicating non-compliance with the established workflow.

Example 11 includes the subject matter of Example 10, wherein the work area is a patient room of a healthcare facility, and the predetermined temporal sequence of the RF signals associated with the established workflow comprises: at least one RF signal representing all of a plurality of hand sanitizing station RFID tags each mounted proximally to a hand sanitizing station located within the patient room; followed by at least one RF signal representing fewer than all of the hand sanitizing station RFID tags over at least a predetermined period of time.

Example 12 includes the subject matter of Example 11, wherein the work area is a patient room of a healthcare facility, and the predetermined temporal sequence of the RF signals associated with the established workflow further comprises at least one RF signal representing a staff member RFID tag associated with a healthcare facility staff member prior to the at least one RF signal representing fewer than all of the hand sanitizing station RFID tags.

Example 13 includes the subject matter of any of Examples 1-12, wherein the warning condition exists while the temporal sequence of the RF signals detected by the RF sensor is the same as the predetermined temporal sequence of the RF signals associated with the established workflow.

Example 14 includes the subject matter of Example 13, wherein the work area is a patient room of a healthcare facility, and the predetermined temporal sequence of RF signals associated with the established workflow comprises: at least one RF signal representing any of a plurality of intravenous solution dispenser RFID tags each mounted proximally to an intravenous solution dispenser located within the patient room; followed by at least one RF signal representing all except one of the intravenous solution dispenser RFID tags.

Example 15 is a method for providing an early warning of non-compliance with an established workflow in a work area. The method comprises: detecting, by a radio frequency (RF) sensor, each of a plurality of RF signals located within the work area; comparing, by a monitoring system operably connected to the RF sensor, a temporal sequence of the RF signals detected by the RF sensor to a predetermined temporal sequence of the RF signals associated with the established workflow; and determining, by the monitoring system, that a warning condition exists based on the comparison.

Example 16 includes the subject matter of Example 15, further comprising: causing, by the monitoring system, a warning indicator operably connected to the monitoring system to generate at least one of a human-perceptible audible cue and a human-perceptible visual cue in response to determining that the warning condition exists.

Example 17 includes the subject matter of any of Examples 15 and 16, wherein the warning condition exists while the temporal sequence of the RF signals detected by the RF sensor differs from the predetermined temporal sequence of the RF signals associated with the established workflow.

Example 18 includes the subject matter of Example 17, wherein the work area is a patient room of a healthcare facility, and wherein the predetermined temporal sequence of the RF signals associated with the established workflow comprises: at least one RF signal representing all of a plurality of hand sanitizing station radio frequency identification (RFID) tags each mounted proximally to a hand sanitizing station located within the patient room; followed by at least one RF signal representing fewer than all of the hand sanitizing station RFID tags over at least a predetermined period of time.

Example 19 includes the subject matter of Example 18, wherein the predetermined temporal sequence of the RF signals associated with the established workflow further comprises at least one RF signal representing a staff member RFID tag associated with a healthcare facility staff member prior to the at least one RF signal representing fewer than all of the hand sanitizing station RFID tags.

Example 20 includes the subject matter of any of Examples 15-19, wherein the warning condition exists while the temporal sequence of the RF signals detected by the RF sensor is the same as the predetermined temporal sequence of the RF signals associated with the established workflow.

Example 21 includes the subject matter of Example 20, wherein the work area is a patient room of a healthcare facility, and wherein the predetermined temporal sequence of RF signals associated with the established workflow comprises: at least one RF signal representing any of a plurality of intravenous solution dispenser radio frequency identification (RFID) tags each mounted proximally to an intravenous solution dispenser located within the patient room; followed by at least one RF signal representing all except one of the intravenous solution dispenser RFID tags.

Example 22 is a non-transitory computer program product having instructions encoded thereon that when executed by one or more computer processors cause the one or more computer processors to perform a process comprising: receiving, from a radio frequency (RF) sensor, each of a plurality of RF signals detected within a work area; comparing a temporal sequence of the RF signals to a predetermined temporal sequence of the RF signals associated with an established workflow; and determining that a warning condition exists based on the comparison.

Example 23 includes the subject matter of Example 22, wherein the process further comprises: causing a warning indicator to generate at least one of a human-perceptible audible cue and a human-perceptible visual cue in response to determining that the warning condition exists.

Example 24 includes the subject matter of any of Examples 22 and 23, wherein the warning condition exists while the temporal sequence of the RF signals detected by the RF sensor differs from the predetermined temporal sequence of the RF signals associated with the established workflow.

Example 25 includes the subject matter of Example 24, wherein the work area is a patient room of a healthcare facility, and wherein the predetermined temporal sequence of the RF signals associated with the established workflow comprises: at least one RF signal representing all of a plurality of hand sanitizing station radio frequency identification (RFID) tags each mounted proximally to a hand sanitizing station located within the patient room; followed by at least one RF signal representing fewer than all of the hand sanitizing station RFID tags over at least a predetermined period of time.

Example 26 includes the subject matter of Example 25, wherein the predetermined temporal sequence of the RF signals associated with the established workflow further comprises at least one RF signal representing a staff member RFID tag associated with a healthcare facility staff member prior to the at least one RF signal representing fewer than all of the hand sanitizing station RFID tags.

Example 27 includes the subject matter of any of Examples 22-26, wherein the warning condition exists while the temporal sequence of the RF signals detected by the RF sensor is the same as the predetermined temporal sequence of the RF signals associated with the established workflow.

Example 28 includes the subject matter of Example 27, wherein the work area is a patient room of a healthcare facility, and wherein the predetermined temporal sequence of RF signals associated with the established workflow comprises: at least one RF signal representing any of a plurality of intravenous solution dispenser radio frequency identification (RFID) tags each mounted proximally to an intravenous solution dispenser located within the patient room; followed by at least one RF signal representing all except one of the intravenous solution dispenser RFID tags.

Example 29 is an early warning system for compliance with an established workflow in a work area. The system comprises: means for detecting each of a plurality of radio frequency (RF) signals located within the work area; and a monitoring system operably connected to the means for detecting the RF signals, the monitoring system configured to: compare a temporal sequence of the RF signals to a predetermined temporal sequence of the RF signals associated with the established workflow; and determine whether a warning condition exists based on the comparison.

Example 30 includes the subject matter of Example 29, further comprising means for generating a cue including at least one of a human-perceptible audible cue and a human-perceptible visual cue, wherein the monitoring system is further configured to cause the means for generating the cue to generate the cue in response to determining that the warning condition exists.

Example 31 includes the subject matter of any of Examples 29 and 30, wherein the warning condition exists while the temporal sequence of the RF signals differs from the predetermined temporal sequence of the RF signals associated with the established workflow.

Example 32 includes the subject matter of Example 31, wherein the work area is a patient room of a healthcare facility, and wherein the predetermined temporal sequence of the RF signals associated with the established workflow comprises: at least one RF signal representing all of a plurality of sanitizing station radio frequency identification (RFID) tags each mounted proximally to a hand sanitizing station located within the patient room; followed by at least one RF signal representing fewer than all of the hand sanitizing station RFID tags over at least a predetermined period of time.

Example 33 includes the subject matter of Example 32, wherein the predetermined temporal sequence of the RF signals associated with the established workflow further comprises at least one RF signal representing a staff member RFID tag associated with a healthcare facility staff member prior to the at least one RF signal representing fewer than all of the hand sanitizing station RFID tags.

Example 34 includes the subject matter of any of Examples 29-33, wherein the warning condition exists while the temporal sequence of the RF signals is the same as the predetermined temporal sequence of the RF signals associated with the established workflow.

Example 35 includes the subject matter of Example 34, wherein the work area is a patient room of a healthcare facility, and wherein the predetermined temporal sequence of RF signals associated with the established workflow comprises: at least one RF signal representing any of a plurality of intravenous solution dispenser radio frequency identification (RFID) tags each mounted proximally to an intravenous solution dispenser located within the patient room; followed by at least one RF signal representing all except one of the intravenous solution dispenser RFID tags.

The foregoing description of example embodiments is presented for the purposes of illustration and description. It is not intended to be exhaustive or to limit this disclosure to the precise forms described. Many modifications and variations are possible in light of this disclosure. It is intended that the scope of the present disclosure be limited not be this detailed description, but rather by the claims appended hereto. Future filed applications claiming priority to this application may claim the disclosed subject matter in a different manner, and may generally include any set of one or more elements as variously disclosed or otherwise demonstrated herein.

What is claimed is:

1. An early warning system for non-compliance with an established workflow in a work area, the system comprising:
 a radio frequency (RF) sensor configured to detect each of a plurality of RF signals within the work area; and
 a monitoring system operably connected to the RF sensor, the monitoring system configured to
  compare a temporal sequence of at least two different RF signals detected by the RF sensor to a predetermined temporal sequence of the RF signals associated with the established workflow; and
  determine whether a warning condition exists based on the comparison.

2. The system of claim 1, further comprising at least one radio frequency identification (RFID) tag configured to emit at least one of the RF signals detectable by the RF sensor.

3. The system of claim 2, wherein the at least one RFID tag is one of an ultra-high frequency (UHF) RFID tag, a high frequency (HF) RFID tag, and a low frequency (LF) RFID tag.

4. The system of claim 2, wherein the work area is a patient room of a healthcare facility, and the at least one RFID tag comprises at least one hand sanitizing station RFID tag mounted proximally to a hand sanitizing station located within the patient room.

5. The system of claim 4, wherein the at least one hand sanitizing station RFID tag is mounted on one of a wall of the patient room and a floor of the patient room.

6. The system of claim 2, wherein the work area is a patient room of a healthcare facility, and the at least one RFID tag comprises at least one intravenous solution RFID tag mounted proximally to an intravenous solution dispenser located within the patient room.

7. The system of claim 6, wherein the intravenous solution RFID tag is attached to a side of the intravenous solution dispenser.

8. The system of claim 2, wherein the work area is a patient room of a healthcare facility, and the at least one RFID tag comprises a staff member RFID tag associated with a healthcare facility staff member and configured to be carried by the staff member while the staff member occupies the patient room.

9. The system of claim 1, further comprising a warning indicator operably connected to the monitoring system and configured to generate a cue including at least one of a human-perceptible audible cue and a human-perceptible visual cue, wherein the monitoring system is further configured to cause the warning indicator to generate the cue in response to determining that the warning condition exists.

10. The system of claim 1, wherein the warning condition exists while the temporal sequence of the RF signals detected by the RF sensor differs from the predetermined temporal sequence of the RF signals associated with the established workflow, thereby indicating non-compliance with the established workflow.

11. The system of claim 10, wherein the work area is a patient room of a healthcare facility, and the predetermined temporal sequence of the RF signals associated with the established workflow comprises:
   at least one RF signal representing all of a plurality of hand sanitizing station RFID tags each mounted proximally to a hand sanitizing station located within the patient room; followed by
   at least one RF signal representing fewer than all of the hand sanitizing station RFID tags over at least a predetermined period of time.

12. The system of claim 11, wherein the work area is a patient room of a healthcare facility, and the predetermined temporal sequence of the RF signals associated with the established workflow further comprises at least one RF signal representing a staff member RFID tag associated with a healthcare facility staff member prior to the at least one RF signal representing fewer than all of the hand sanitizing station RFID tags.

13. The system of claim 1, wherein the warning condition exists while the temporal sequence of the RF signals detected by the RF sensor is the same as the predetermined temporal sequence of the RF signals associated with the established workflow.

14. The system of claim 13, wherein the work area is a patient room of a healthcare facility, and the predetermined temporal sequence of RF signals associated with the established workflow comprises:
   at least one RF signal representing any of a plurality of intravenous solution dispenser RFID tags each mounted proximally to an intravenous solution dispenser located within the patient room; followed by
   at least one RF signal representing all except one of the intravenous solution dispenser RFID tags.

15. A method for providing an early warning of non-compliance with an established workflow in a work area, the method comprising:
   detecting, by a radio frequency (RF) sensor, each of a plurality of RF signals located within the work area;
   comparing, by a monitoring system operably connected to the RF sensor, a temporal sequence of at least two different RF signals detected by the RF sensor to a predetermined temporal sequence of the RF signals associated with the established workflow; and
   determining, by the monitoring system, that a warning condition exists based on the comparison.

16. The method of claim 15, further comprising:
   causing, by the monitoring system, a warning indicator operably connected to the monitoring system to generate at least one of a human-perceptible audible cue and a human-perceptible visual cue in response to determining that the warning condition exists.

17. The method of claim 15, wherein the warning condition exists while the temporal sequence of the RF signals detected by the RF sensor differs from the predetermined temporal sequence of the RF signals associated with the established workflow.

18. The method of claim 17, wherein the work area is a patient room of a healthcare facility, and wherein the predetermined temporal sequence of the RF signals associated with the established workflow comprises:
   at least one RF signal representing all of a plurality of hand sanitizing station radio frequency identification (RFID) tags each mounted proximally to a hand sanitizing station located within the patient room; followed by
   at least one RF signal representing fewer than all of the hand sanitizing station RFID tags over at least a predetermined period of time.

19. The method of claim 18, wherein the predetermined temporal sequence of the RF signals associated with the established workflow further comprises at least one RF signal representing a staff member RFID tag associated with a healthcare facility staff member prior to the at least one RF signal representing fewer than all of the hand sanitizing station RFID tags.

20. The method of claim 15, wherein the warning condition exists while the temporal sequence of the RF signals detected by the RF sensor is the same as the predetermined temporal sequence of the RF signals associated with the established workflow.

21. The method of claim 20, wherein the work area is a patient room of a healthcare facility, and wherein the predetermined temporal sequence of RF signals associated with the established workflow comprises:
   at least one RF signal representing any of a plurality of intravenous solution dispenser radio frequency identification (RFID) tags each mounted proximally to an intravenous solution dispenser located within the patient room; followed by
   at least one RF signal representing all except one of the intravenous solution dispenser RFID tags.

22. A non-transitory computer program product having instructions encoded thereon that when executed by one or more computer processors cause the one or more computer processors to perform a process comprising:
- receiving, from a radio frequency (RF) sensor, each of a plurality of RF signals detected within a work area;
- comparing a temporal sequence of at least two different RF signals to a predetermined temporal sequence of the RF signals associated with an established workflow; and
- determining that a warning condition exists based on the comparison.

23. The non-transitory computer program product of claim 22, wherein the process further comprises:
- causing a warning indicator to generate at least one of a human-perceptible audible cue and a human-perceptible visual cue in response to determining that the warning condition exists.

24. The non-transitory computer program product of claim 22, wherein the warning condition exists while the temporal sequence of the RF signals detected by the RF sensor differs from the predetermined temporal sequence of the RF signals associated with the established workflow.

25. The non-transitory computer program product of claim 22, wherein the warning condition exists while the temporal sequence of the RF signals detected by the RF sensor is the same as the predetermined temporal sequence of the RF signals associated with the established workflow.

* * * * *